United States Patent
Watson

(10) Patent No.: US 8,636,728 B2
(45) Date of Patent: Jan. 28, 2014

(54) APPARATUS AND METHODS FOR RETRACTING A CATHETER BALLOON

(75) Inventor: James R. Watson, Santa Rosa, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 957 days.

(21) Appl. No.: 12/711,119

(22) Filed: Feb. 23, 2010

(65) Prior Publication Data

US 2010/0234838 A1  Sep. 16, 2010

Related U.S. Application Data

(60) Provisional application No. 61/159,375, filed on Mar. 11, 2009.

(51) Int. Cl.
*A61B 18/02* (2006.01)

(52) U.S. Cl.
USPC .............................. 606/21; 606/191

(58) Field of Classification Search
USPC .......... 606/7, 21, 23, 75, 193, 195, 196; 604/917, 920, 509, 103.05; 623/1.23; 600/115, 116, 207, 470
See application file for complete search history.

(56) References Cited

U.S. PATENT DOCUMENTS

| | | | | |
|---|---|---|---|---|
| 2,490,364 A | * | 12/1949 | Livingston | 606/68 |
| 5,611,688 A | * | 3/1997 | Hanosh | 433/174 |
| 5,725,529 A | * | 3/1998 | Nicholson et al. | 606/232 |
| 5,782,865 A | * | 7/1998 | Grotz | 606/232 |
| 5,846,238 A | | 12/1998 | Jackson et al. | |
| 6,106,518 A | | 8/2000 | Wittenberger et al. | |
| 6,780,183 B2 | | 8/2004 | Jimenez, Jr. et al. | |
| 2003/0040703 A1 | * | 2/2003 | Rauker et al. | 604/96.01 |

* cited by examiner

*Primary Examiner* — Michael Peffley
*Assistant Examiner* — Thomas Giuliani
(74) *Attorney, Agent, or Firm* — Seager, Tufte & Wickhem, LLC

(57) ABSTRACT

A balloon elongation apparatus includes an elongated hypotube with a distal end having a reduced inner diameter portion that is configured to radially expand when a mandrel is advanced through a lumen of the hypotube towards the reduced inner diameter portion. A medical kit includes a catheter having a distally-located balloon and the elongation apparatus disposed within a guide wire tube of the catheter. In use, the balloon is elongated following a procedure in order to facilitate retracting the balloon into a sheath. The balloon is elongated by first advancing the mandrel relative to the hypotube so that the hypotube radially expands and firmly engages an inner surface of the guide wire tube and then advancing the mandrel, hypotube, and distal end of the guide wire tube relative to the catheter body.

3 Claims, 11 Drawing Sheets

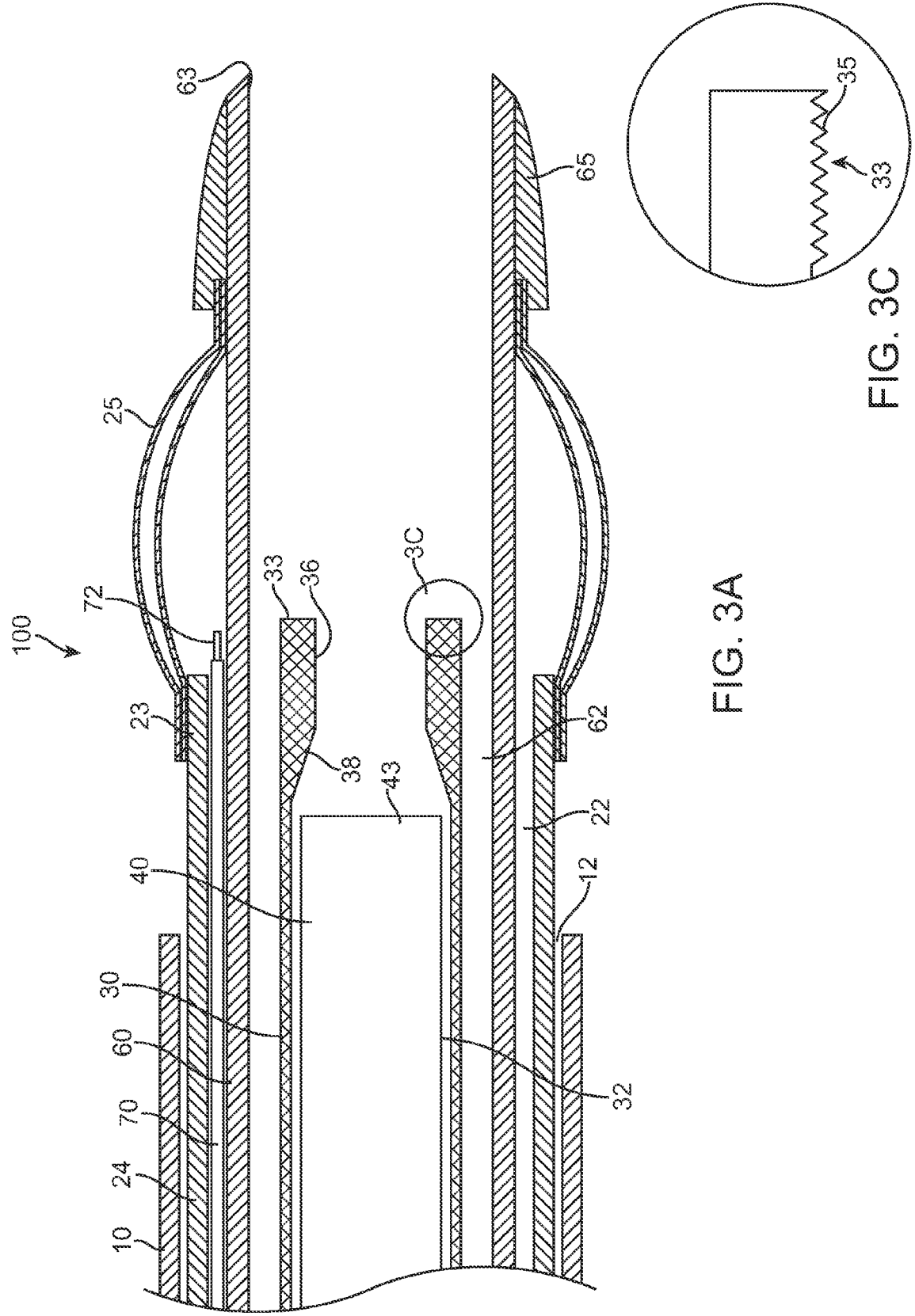

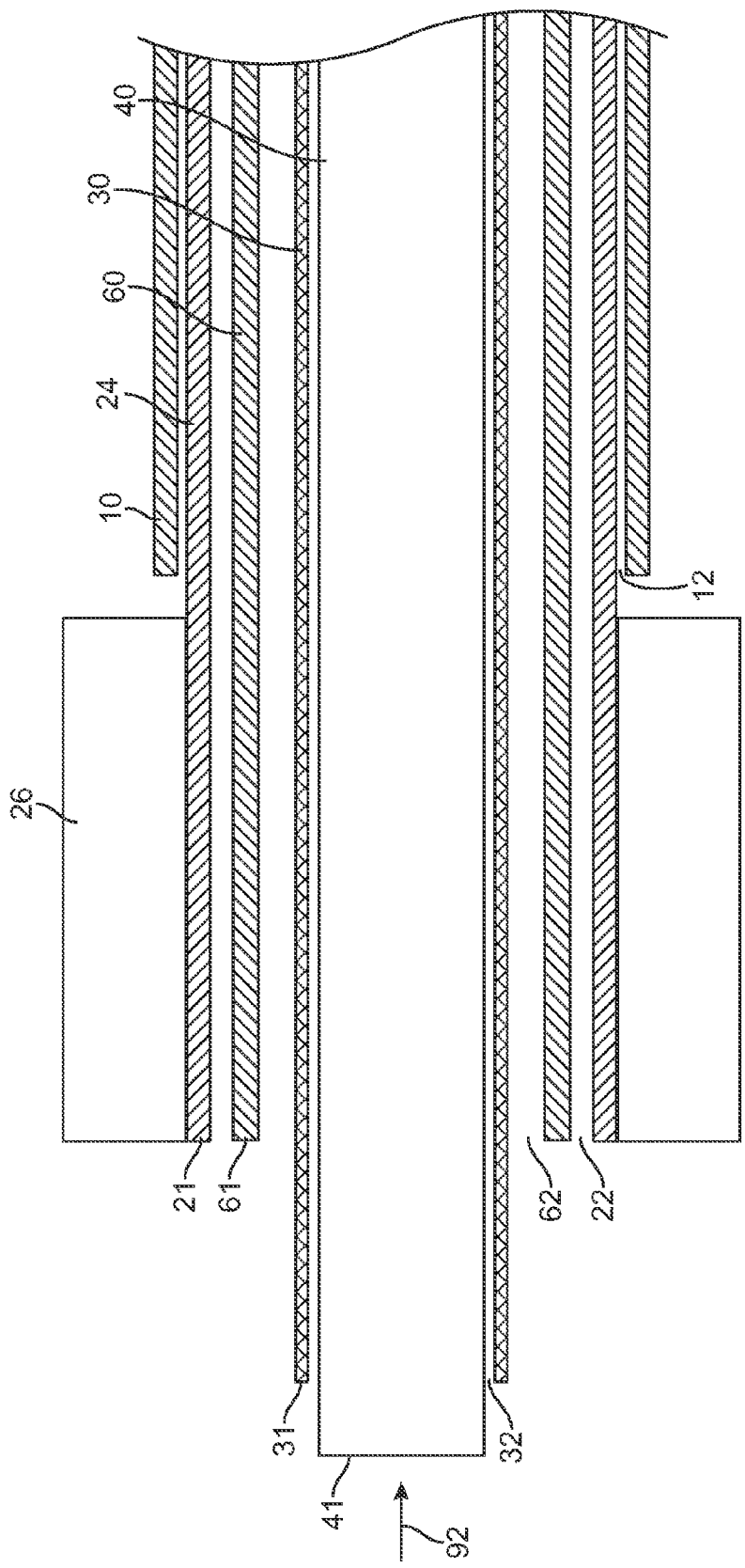

APPARATUS AND METHODS FOR RETRACTING A CATHETER BALLOON

RELATED APPLICATION DATA

The present application claims the benefit under 35 U.S.C. §119 to U.S. provisional patent application Ser. No. 61/159,375, filed Mar. 11, 2009. The foregoing application is hereby incorporated by reference into the present application in its entirety.

FIELD OF THE INVENTION

The disclosed inventions relate to apparatus and methods for retracting a catheter balloon within the distal end of a sheath.

BACKGROUND

Atrial fibrillation is a condition in which upper chambers of the heart beat rapidly and irregularly. One known manner of treating atrial fibrillation is to administer drugs in order to maintain normal sinus rhythm and/or to decrease ventricular rhythm. Known drug treatments, however, may not be sufficiently effective, and additional measures such as cardiac tissue ablation must often be taken to control the arrhythmia.

Known ablation procedures for treating atrial fibrillation include performing transmural ablation of the heart wall or adjacent tissue walls using radio frequency (RF) energy. One known ablation procedure involves burning or ablating cardiac tissue and forming lesions to break up circuits believed to drive atrial fibrillation.

The use of RF energy for ablation may, however, lead to untoward healing responses such as collagen build up at the area of interest after treatment. RF ablation within an atrium may also decrease atrial output. Thus, while RF transmural ablation has been used effectively in the past, cryogenic ablation has received increased attention for treatment of atrial fibrillation in view of the effectiveness of cryo-ablation procedures with fewer side effects.

One known endocardial cryo-ablation procedure involves inserting a catheter into the heart, e.g., through the leg of a patient. Once properly positioned, a portion of the catheter, typically the tip of the catheter, is cooled to a sufficiently low temperature by use of a liquid coolant or refrigerant such as nitrous oxide, e.g., to sub-zero temperatures of about −75° C., in order to freeze tissue believed to conduct signals that cause atrial fibrillation. The frozen tissue eventually dies so that the ablated tissue no longer conducts electrical impulses that are believed to cause or conduct atrial fibrillation signals.

Certain known endocardial cryo-ablation devices include expandable balloons, which are inflated with the liquid coolant or refrigerant. After the ablation is performed and before the device is withdrawn from the patient, the balloon is deflated and retracted into a guide sheath.

However, after expanding the balloon, performing the ablation procedure, and deflating the balloon, a user may encounter difficulties in retracting the deflated balloon into the guide sheath due to the balloon having a profile that is too large to re-enter the sheath. In particular, prior to inflation, the balloon profile is at its smallest, but after inflation has occurred, the balloon material is free to expand and may bunch up at the tip of the sheath during retraction of the balloon into the sheath. Thus, increased force is required to retract the deflated balloon, thereby potentially damaging the balloon during the balloon retraction procedure.

SUMMARY OF THE DISCLOSED INVENTIONS

In accordance with a first aspect of the disclosed inventions, a balloon elongation apparatus is provided. The balloon elongation apparatus includes an elongated member sized to fit within a guide wire lumen of a catheter. The elongated member has a proximal end, a distal end configured to be placed between a radially expanded configuration to firmly engage an inner surface of the guide wire lumen, and a radially relaxed configuration to slide within the guide wire lumen, a lumen extending between the proximal end and the distal end, a larger inner diameter portion, and a smaller inner diameter portion distal to the larger inner diameter portion.

In one embodiment, the elongated member includes a tapered transition region between the smaller inner diameter portion and the larger inner diameter portion. In another embodiment, the distal end of the elongated member has a serrated or grooved outer surface. In one embodiment, the balloon elongation apparatus includes an elongated mandrel sized to be slidably received within the larger inner diameter portion of the elongated member and configured for radially expanding the distal end of the elongated member when a distal end of the mandrel is advanced from the larger inner diameter portion towards the smaller inner diameter portion.

In accordance with another aspect of the disclosed inventions, a medical kit is provided. The medical kit includes a catheter body having a proximal end and a distal end. The medical kit also includes a guide wire tube having a proximal end, a distal end, and a lumen extending between the proximal end and the distal end. The guide wire tube extends through the catheter body, such that the distal end of the guide wire tube extends from the distal end of the catheter body. The medical kit further includes an expandable balloon (e.g., a tissue ablation balloon) having a proximal end mounted to the distal end of the catheter body and a distal end mounted to the distal end of the guide wire tube. The medical kit also includes a balloon elongation apparatus configured for extending through the lumen of the guide wire tube and for distally advancing the distal end of the guide wire tube relative to the distal end of the catheter body, thereby elongating the balloon.

In one embodiment, the balloon elongation apparatus includes an elongated mandrel and an elongated member sized to fit within the lumen of the guide wire tube. The details of the elongated member may be the same as those described above. In one embodiment, the medical kit includes a guide wire configured for extending through the lumen of the guide wire tube, wherein the balloon elongation apparatus is configured for being exchanged with the guide wire within the lumen of the guide wire tube. The medical kit may also include a delivery sheath having a lumen in which the catheter body is disposed, wherein the balloon, when deflated, is configured for being retracted within the lumen of the sheath.

In accordance with still another aspect of the disclosed inventions, a method for performing a medical procedure (e.g., a cryogenic ablation procedure) on a patient using a catheter having a distally-located expandable body (e.g., a balloon) is provided. The method includes introducing a delivery sheath into the patient, advancing the catheter through the sheath until the expandable body distally deploys out from the sheath, placing the expandable body into an expanded geometry, operating the expandable body to perform the medical procedure on the patient, and placing the expandable body into a collapsed geometry after performing the medical procedure. Thereafter, the method includes inserting an elongated member into a lumen of the catheter. In one embodiment, the lumen of the catheter is a guide wire lumen within a catheter body. The elongated member may be inserted into the guide wire lumen such that the distal end of the elongated member is proximal to the distal end of the guide wire lumen, and a proximal end of the elongated member extends from a proximal end of the guide wire lumen. In one embodiment, the method includes removing a guide wire from the lumen before inserting the elongated member into the lumen.

In one exemplary method, after inserting the elongated member into the guide wire lumen, the method further includes radially expanding a distal end of the elongated member to firmly engage an inner surface of the guide wire lumen. The distal end of the elongated member may be radially expanded by distally advancing an elongated mandrel within a lumen of the elongated member. In one embodiment, distally advancing the mandrel may include advancing a distal end of the mandrel from a larger inner diameter portion of the elongated member into a smaller inner diameter portion of the elongated member. Prior to the radially expanding, the mandrel may be inserted into the lumen of the elongated member such that a proximal end of the mandrel extends from a proximal end of the elongated member and a distal end of the mandrel is proximal to the distal end of the elongated member. The method further includes distally advancing the elongated member within the lumen to elongate the expandable body when in the collapsed geometry, and retracting the elongated expandable body into the sheath. The elongated member may be distally advanced to elongate the expandable body by advancing a distal end of the guide wire lumen relative to a distal end of the catheter body.

BRIEF DESCRIPTION OF THE DRAWINGS

Referring now to the drawings in which like reference numbers represent corresponding parts throughout and in which:

FIGS. 3A and 3B are cross-sectional views of the distal end and the proximal end, respectively, of the medical kit assembly with the elongation apparatus disposed within the catheter in place of the guide wire;

FIG. 3C is a detailed view of the portion of the elongated hypotube in FIG. 3A;

DETAILED DESCRIPTION OF ILLUSTRATED EMBODIMENTS

Embodiments relate to apparatus and methods for placing a deflated balloon into a smaller profile such that the balloon may easily be retracted into a sheath and safely removed from a patient's body. In this manner, embodiments advantageously elongate the balloon after deflation such that the deflated balloon has a smaller profile than known devices, which may encounter difficulty in retracting the deflated balloon. Embodiments are described in further detail with reference to FIG. 1, which illustrates a medical kit including a balloon elongation apparatus, FIGS. 2, 3A, 3C, 4A, and 5A, which illustrate the distal end of the medical kit during various stages of use, FIGS. 3B, 4B, and 5B, which illustrate the proximal end of the medical kit during various stages of use, and FIGS. 6A-6C, which illustrate some of the steps in a method of using the medical kit to perform a medical procedure. It should be noted that the drawings are not to scale and that several components of the medical kit are depicted as being relatively large or relatively small for illustrative purposes only.

Figure 1:
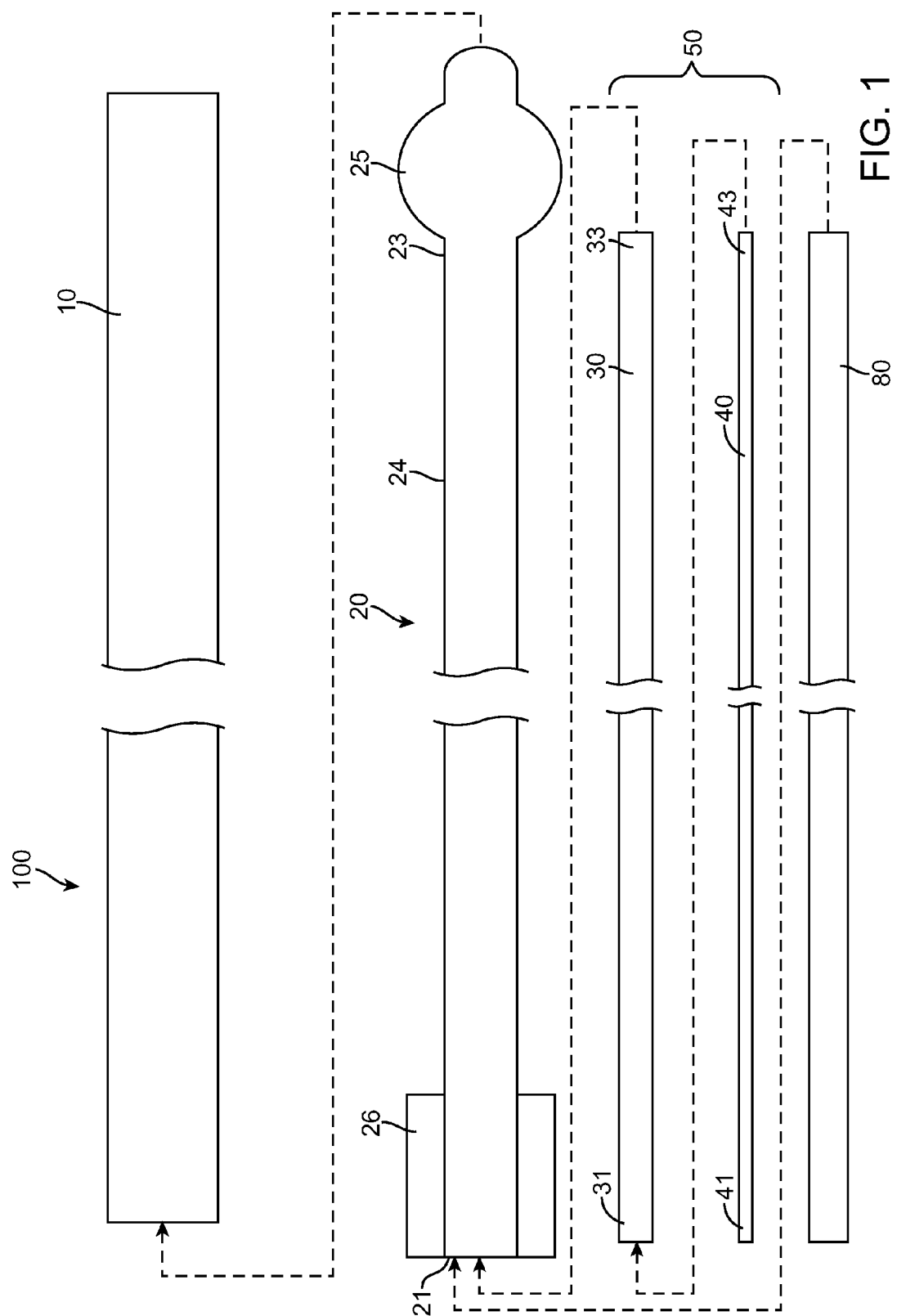
FIG. 1 is an exploded plan view of a medical kit assembly including a balloon elongation apparatus, constructed in accordance with the disclosed inventions.

Referring to FIG. 1, an exemplary medical kit 100 constructed in accordance with the disclosed inventions is shown. The medical kit 100 generally includes a catheter 20 with a distally-located expandable member 25, a guide sheath 10 sized for slidably receiving the catheter 20 therein, and a balloon elongation apparatus 50 sized for being disposed within the catheter 20 and configured for elongating the expandable member 25 prior to retracting the expandable member 25 into the sheath 10, as described in more detail below. The balloon elongation apparatus 50 is advantageously interchangeable with a guide wire 80.

In the illustrated embodiment, the catheter 20 is an ablation catheter comprising a catheter body 24, and the expandable member 25 attached to the distal end 23 of the catheter body 24 is an expandable balloon for use in a cryogenic ablation procedure. It should be noted that, although the balloon elongation apparatus 50 is described as being particularly useful in elongating and retracting an expandable cryogenic ablation balloon 25, the balloon elongation apparatus 50 can also be used in other balloon catheters where it is desirable to elongate the expandable body 25 prior to retracting the expandable body 25 into the sheath 10 or through an opening such as a puncture tract or an opening in an atrial septum.

Figure 2:
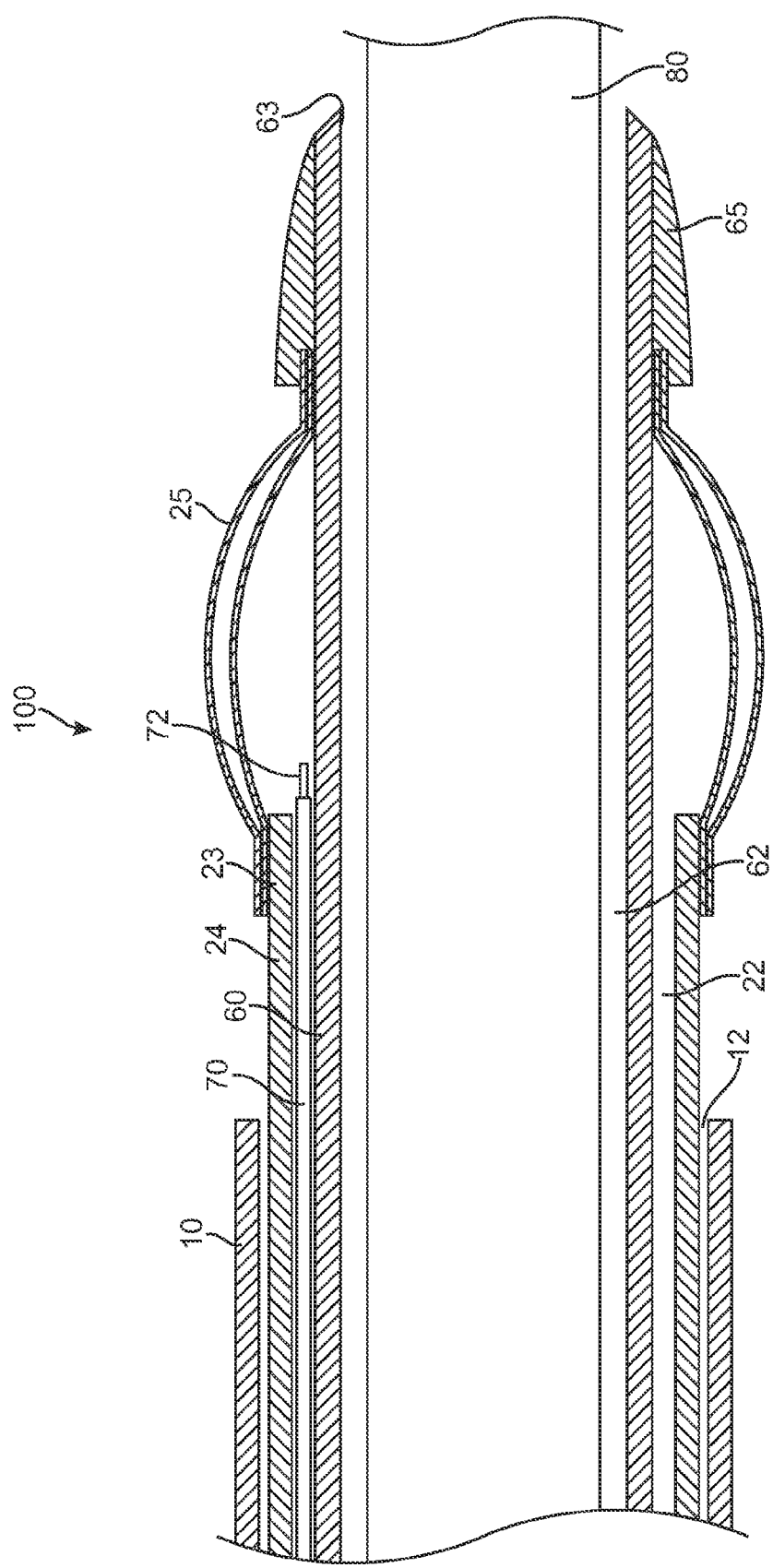
FIG. 2 is a cross-sectional view of the distal end of the medical kit assembly with the guide wire disposed within the catheter before the elongation apparatus is inserted.

As shown in FIG. 2, the catheter 20 also includes a guide wire tube 60, a liquid coolant inlet lumen 72, and a liquid coolant discharge lumen 70 disposed within a lumen 22 of the catheter body 24. The liquid coolant inlet and discharge lumens 72, 70 are disposed between the guide wire tube 60 and the catheter body 24 and extend through the lumen 22 such that the proximal ends (not shown) of the coolant inlet and discharge lumens 72, 70 are coupled to a liquid coolant source and a discharge port, respectively (also not shown), while the distal ends are positioned within the balloon 25. In particular, the distal end of the coolant inlet lumen 72 is positioned within the balloon 25 for flowing liquid coolant into the balloon 25 to thereby inflate the balloon 25 and cryogenically ablate target tissue in contact with the balloon 25 in a conventional manner. The distal end of the coolant discharge lumen 70 is positioned within the balloon for discharging liquid coolant out of the balloon 25 to thereby deflate the balloon 25. Although the inlet and discharge lumens 72, 70 are shown here as concentric lumens, it should be well understood that the inlet lumen 72 and the discharge lumen 70 may have other configurations and may be arranged for more uniform dispersal of the coolant within the balloon 25. For example, the coolant inlet lumen may wind around the guide wire tube for the length of the balloon 25 and have multiple opening for dispersing the coolant liquid throughout the balloon 25.

The guide wire tube 60 extends through the lumen 22 of the catheter body 24 such that the distal end 63 of the guide wire tube 60 extends from the distal end 23 of the catheter body 24, as shown in FIG. 2, while the proximal end 61 of the guide wire tube 60 is even with and fixed relative to the proximal end 21 of the catheter body 24, as shown in FIG. 3B. The guide wire tube 60 may be made of a material that is stretchable (e.g., polyurethane) or relatively inelastic (e.g., nylon). Thus, due to the stretchability of the guide wire tube 60 or to the amount of slack in the guide wire tube 60 relative to the catheter body 24, the distal end 63 of the guide wire tube 60 may be advanced relative to the distal end 23 of the catheter body 24 while the proximal ends 21, 61 of the catheter body 24 and guide wire tube 60 are fixed relative to each other. In the illustrated embodiment, the distal end 63 of the guide wire tube 60 includes a tapered cap 65 for causing less trauma when passing through tissue.

As shown in FIGS. 1, 3B, 4B and 5B, the catheter 20 also includes a handle 26 at the proximal end 21 of the catheter body 24. It should be understood that several elements of the handle 26 are not shown in FIGS. 1, 3B, 4B and 5B for clarity. For example, the handle 26 may include a vacuum port, a vacuum lumen, a coolant inlet port, a coolant inlet lumen, a coolant outlet port, a coolant outlet lumen, and the like.

Although the balloon 25 at the distal end 23 of the catheter body 24 is shown here as a dual balloon, it should be well understood that the balloon 25 may alternatively have other configurations, e.g., a single-walled balloon. In addition, it should be well understood that the space between the balloon walls of the dual balloon 25 is under vacuum and that, for clarity, the vacuum conduit is not illustrated here. The balloon 25 is affixed to both the catheter body 24 and the guide wire tube 60. In particular, the distal end of the balloon 25 is coupled to the distal end 63 of the guide wire tube 60, while the proximal end of the balloon 25 is coupled to the distal end 23 of the catheter body 24. Due to this configuration, movement of the distal end 63 of the guide wire tube 60 relative to the distal end 23 of the catheter body 24 causes the balloon 25 to lengthen or shorten.

The balloon elongation apparatus 50 enables such relative movement between the distal end 63 of the guide wire tube 60 and the distal end 23 of the catheter body 24. To this end, the balloon elongation apparatus 50 includes an elongated member, and in particular, a hypotube 30, and an elongated mandrel 40 sized to be slidably received within a lumen 32 of the hypotube 30. The hypotube 30 is configured to extend through a lumen 62 of the guide wire tube 60, so that the proximal end 31 of the hypotube 30 extends from the proximal end 61 of the guide wire tube 60, as depicted in FIG. 3B, and the distal end 33 of the hypotube 30 is proximal to the distal end 63 of the guide wire tube 60, as depicted in FIG. 3A. Similarly, the mandrel 40 is configured to extend through a lumen 32 of the hypotube 30 so that the proximal end 41 of the mandrel 40 extends from the proximal end 31 of the hypotube 30, as depicted in FIG. 3B, and the distal end 43 of the mandrel 40 is proximal to the distal end 33 of the hypotube 30, as depicted in FIG. 3A. This initial configuration of the assembly 100 allows the mandrel 40 to be distally advanced relative to the hypotube 30 and the hypotube 30 to be distally advanced relative to the catheter body 24 during deployment of the elongation apparatus 50, as discussed in greater detail below.

Substantially the entire length of the hypotube 30 has an inner diameter that is equal to or slightly larger than the outer diameter of the mandrel 40. The distal end 33 of the hypotube 30, however, has a reduced inner diameter. In order to facilitate advancement of the distal end 43 of the mandrel 40 from the larger inner diameter portion 34 towards the smaller inner diameter portion 36, the hypotube 30 includes a tapered transition region 38 between the smaller inner diameter portion 36 and the larger inner diameter portion 34.

As discussed in greater detail below, such advancement of the mandrel 40 relative to the hypotube 30 causes radial expansion of the distal end 33 of the hypotube 30. When the distal end 33 of the hypotube 30 is in the radially expanded configuration, it is firmly engaged to the inner surface of the guide wire tube 60 so that distal advancement of the hypotube 30 causes distal advancement of the distal end 63 of the guide wire tube 60 relative to the distal end 23 of the catheter body 24, thereby elongating the balloon 25. In one embodiment, the outer surface of the distal end 33 of the hypotube 30 has a grooved or serrated surface 35, as shown in FIG. 3C, for facilitating the firm engagement between the distal end 33 and the inner surface of the guide wire tube 60.

Having described the structure of the balloon elongation apparatus 50, the operation of the medical kit assembly 100 in performing an exemplary therapeutic ablation procedure within a left atrium will now be described with reference to FIGS. 2-5 and 6A-6C. Although the method of using the kit 100 is depicted as taking place in the left atrium, the kit 100 is not restricted to use within the left atrium and may advantageously be used in other areas of the body.

Figure 6A:
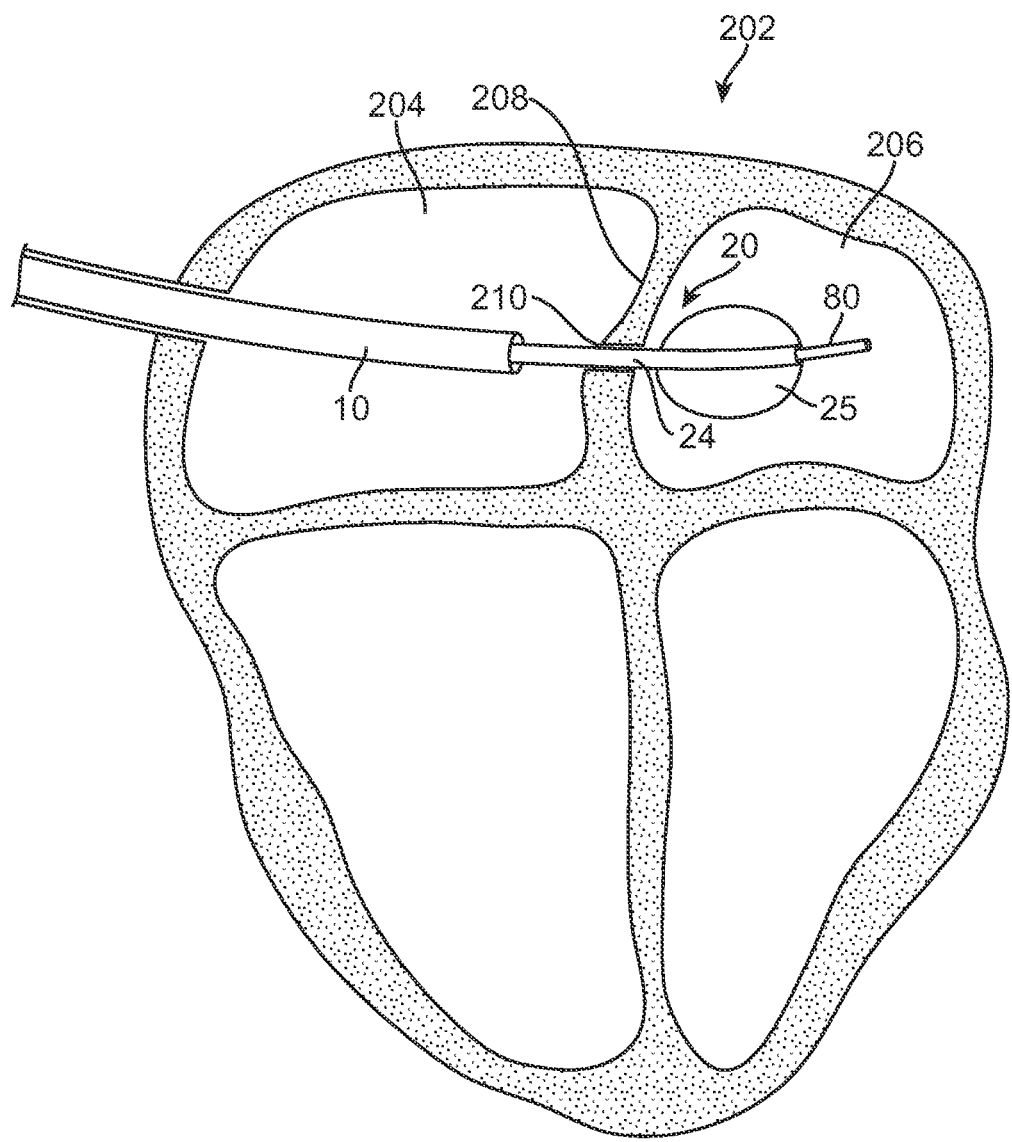
FIGS. 6A-6C are partial cross sectional views of steps in a method of using the medical kit shown in FIG. 1 for performing a medical procedure.

First, the guide sheath 10 is introduced into the right atrium 204 of the heart 202 via the appropriate blood vessel toward the heart 202. The catheter 20 then is advanced through the sheath 10 until the balloon 25 distally deploys out from the sheath 10. The guidewire 80 is inserted through the guide tube 60 of the catheter 20 and advanced, such that the distal end of the guidewire 80 is located at a target site within the left atrium 206 (e.g., a pulmonary vein), and the catheter 20 is further advanced from the right atrium 204 along the guidewire 80 into the left atrium 206 by passing through an opening 210 in the atrial septum 208. Once the catheter 20 is properly positioned within the left atrium 206, liquid coolant flows into the balloon 25 through the coolant inlet lumen 72 to inflate the balloon 25 from its original geometry to an expanded geometry, as shown in FIG. 6A, and an ablation procedure is performed in a conventional manner.

Although the illustrated embodiment depicts a transeptal approach for entering the left atrium 206, it should be well understood that a conventional retrograde approach, i.e., through the respective aortic and mitral valves of the heart, may alternatively be used for entry into the left atrium 206. In addition, it should be well understood that, although the illustrated embodiment depicts the catheter 20 passing through the atrial septum, the sheath 10 may also traverse the atrial septum 208 in the method of using the medical kit 100.

Figure 6B:
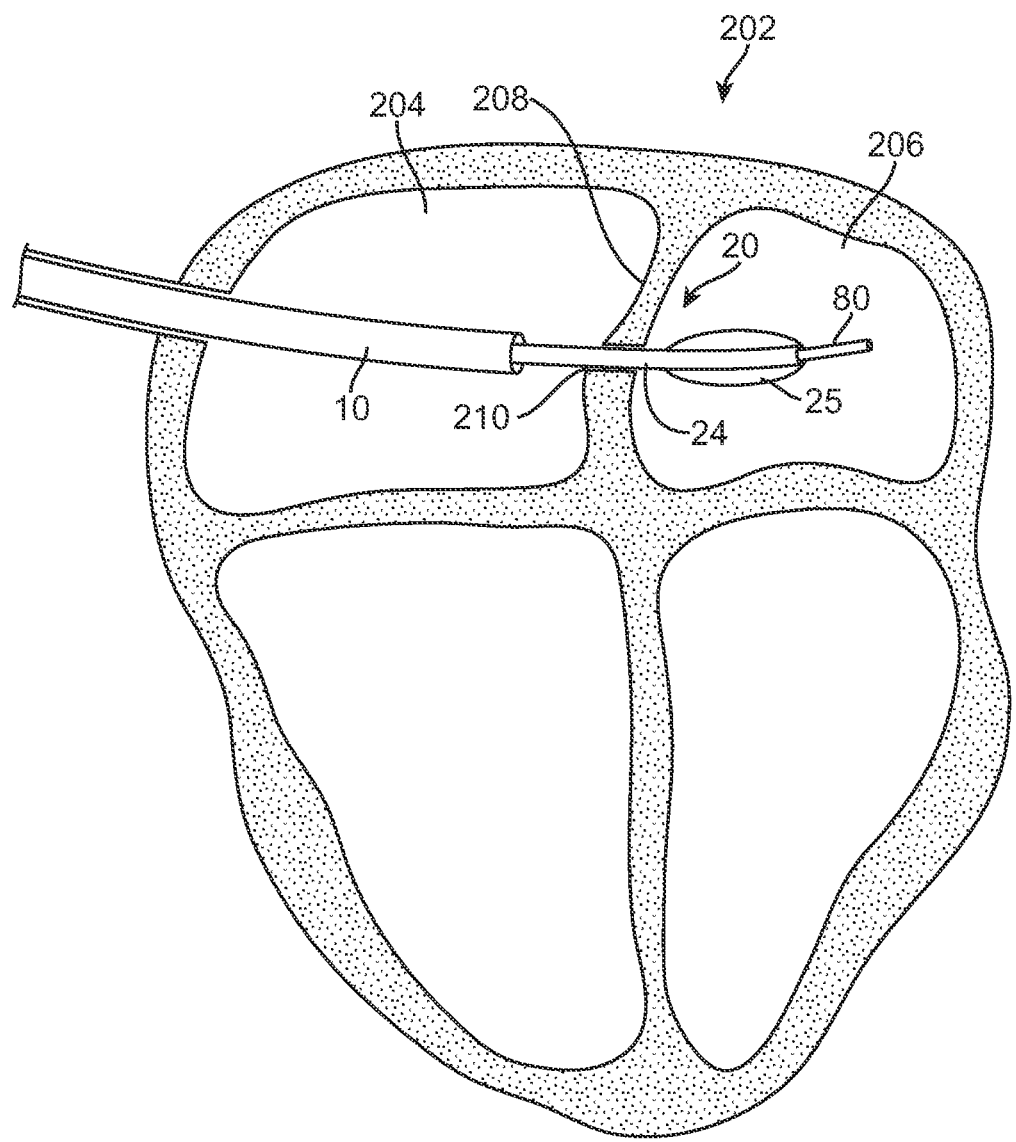

After the ablation procedure is completed and the liquid coolant is discharged from the balloon 25 through the discharge lumen 70, the balloon 25 is deflated (e.g., using vacuum or other conventional deflation procedures) to a collapsed geometry, shown in FIG. 6B, which has a slightly larger profile than the original geometry of the balloon 25 prior to inflation. The distal end of the assembly 100 at this stage of the procedure is illustrated in more detail in FIG. 2. If the balloon 25 in the collapsed configuration has an outer diameter that is larger than the inner diameter of the sheath 10 and/or larger than the opening 210 in the septum 208, it may be difficult to withdraw the balloon 25 back into the sheath 10 and/or back through the opening 210 without tearing or otherwise damaging the balloon 25 and/or the atrial septum 208. Thus, the elongation apparatus 50 may be advantageously used to elongate the balloon 25 to a smaller profile, thereby facilitating withdrawal of the balloon 25 back into the sheath 10 and/or back through the atrial septum 208.

Prior to deploying the elongation apparatus 50, the guide wire 80 is exchanged for the elongation apparatus 50. Thus, the guide wire 80 is proximally withdrawn from the guide wire tube 60 and the hypotube 30 is inserted into the guide wire tube 60. If the mandrel 40 is not already predisposed in the hypotube 30, the mandrel 40 is then inserted into the lumen 32 of the hypotube 30. As shown in FIG. 3A, the distal end 43 of the mandrel 40 is proximal to the distal end 33 of the hypotube 30 and the distal end 33 of the hypotube 30 is proximal to the distal end 63 of the guide wire tube 60. As shown in FIG. 3B, the proximal end 41 of the mandrel protrudes from the proximal end 31 of the hypotube 30, which protrudes from the proximal ends 21, 61 of the catheter body 24 and guide wire tube 60.

Figure 4A:
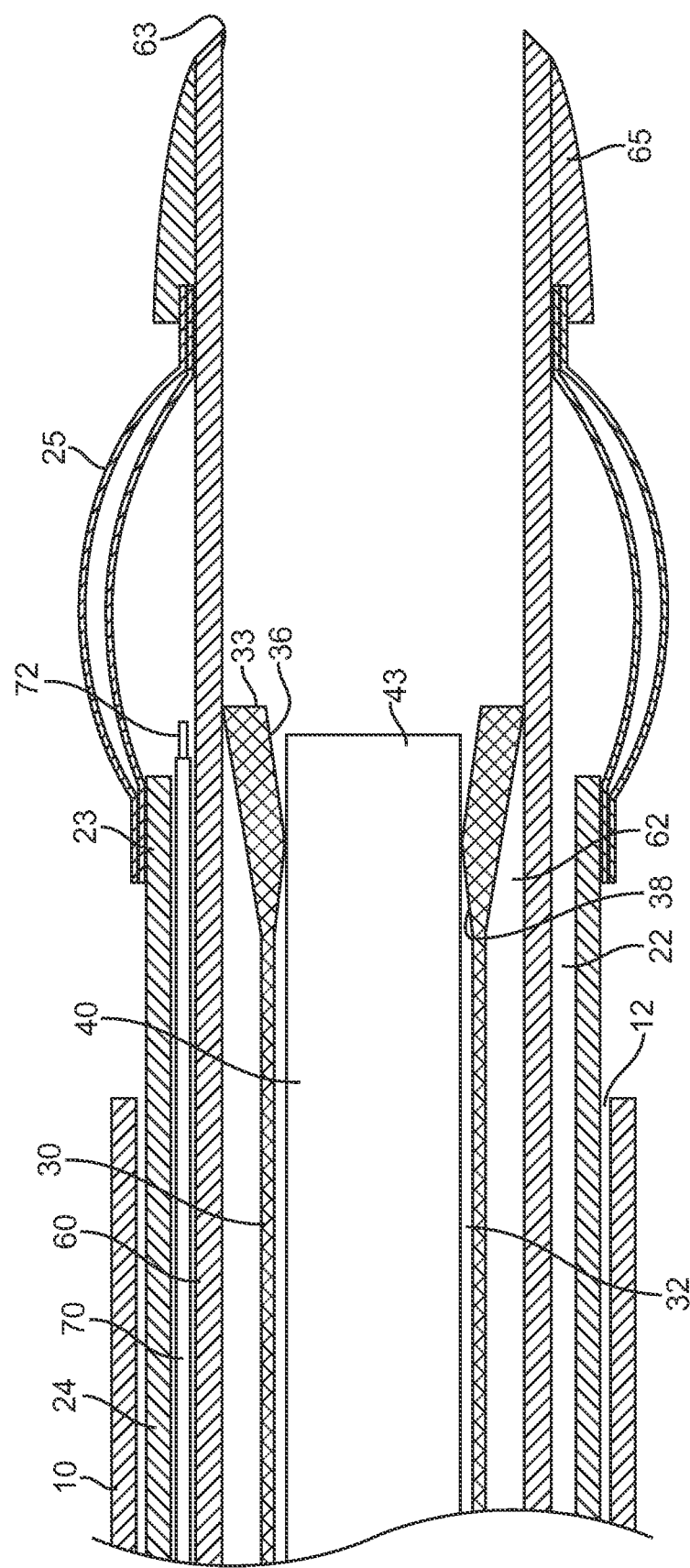
FIGS. 4A and 4B are cross-sectional views of the distal end and the proximal end, respectively, of the medical kit assembly during a first step of deployment of the elongation apparatus.
Figure 4B:
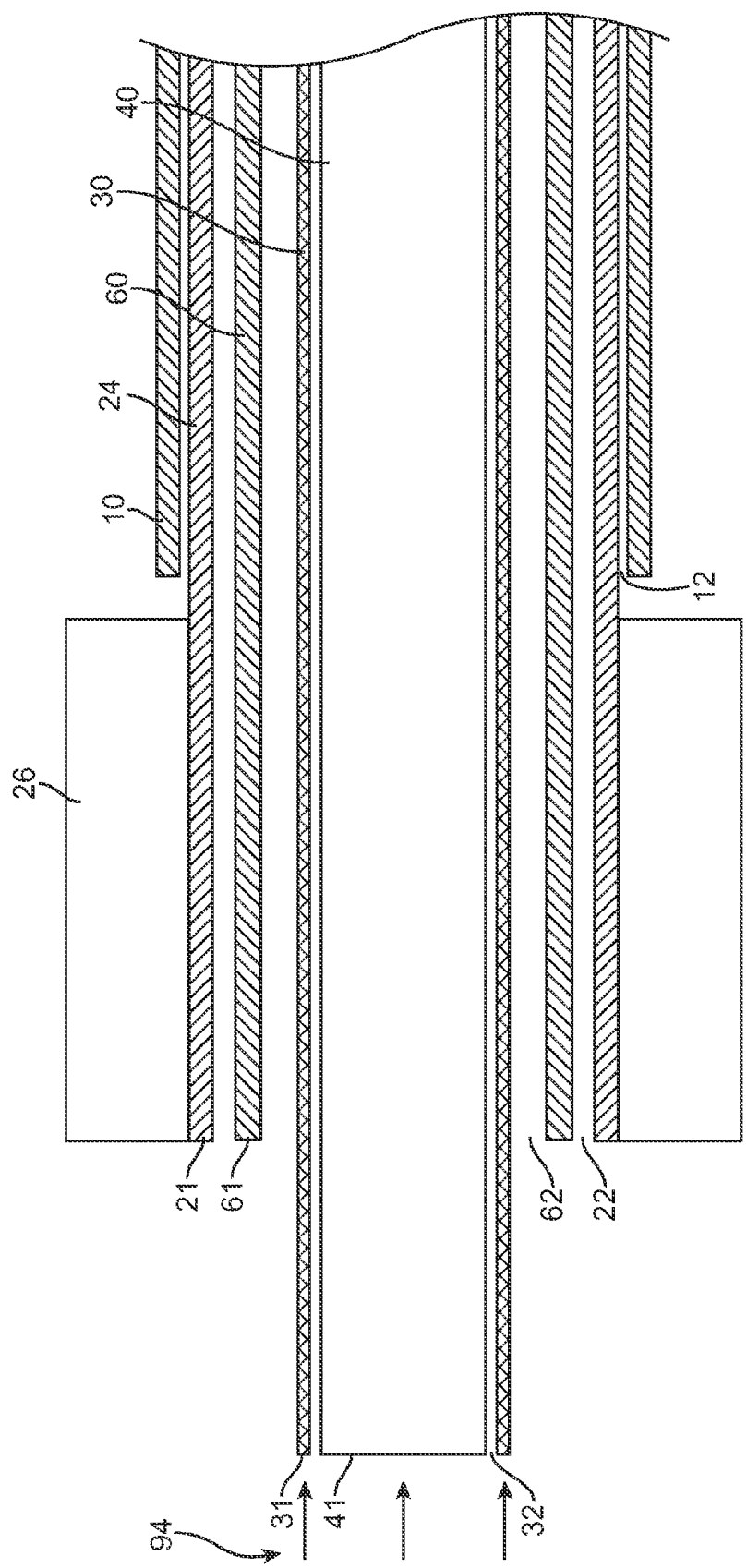

In a first stage of deploying the elongation apparatus 50, the mandrel 40 is advanced distally relative to the hypotube 30, as indicated by arrow 92 in FIG. 3B. As a result, the distal end 33 of the hypotube 30 radially expands and firmly engages the inner surface of the guide wire tube 60, as depicted in FIG. 4A. As the mandrel 40 is advanced, the distal end 43 of the mandrel 40 moves through the larger inner diameter portion 34 and slides along the transition region 38 of the inner surface of the hypotube 30 into the smaller inner diameter portion 36. The mandrel 40 is advanced until the proximal end 41 is flush with the proximal end 31 of the hypotube 30, as shown in FIG. 4B. Alternatively, it should be well understood that the mandrel 40 may be advanced a predetermined distance by including a marker (not shown) on the shaft of the mandrel 40 and advancing the mandrel 40 distally until the marker reaches a desired location, e.g., the proximal end 31 of the hypotube 30.

Figure 5A:
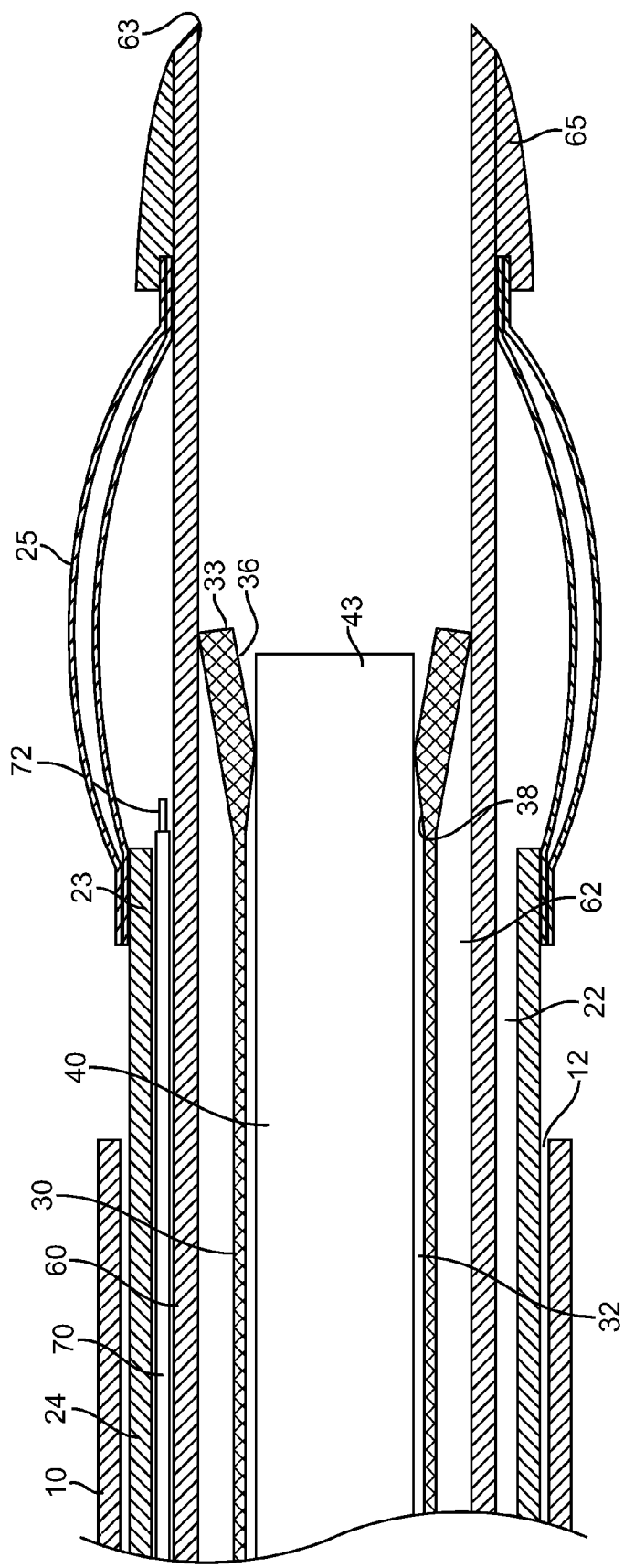
FIGS. 5A and 5B are cross-sectional views of the distal end and the proximal end, respectively, of the medical kit assembly during a second step of deployment of the elongation apparatus.
Figure 5B:
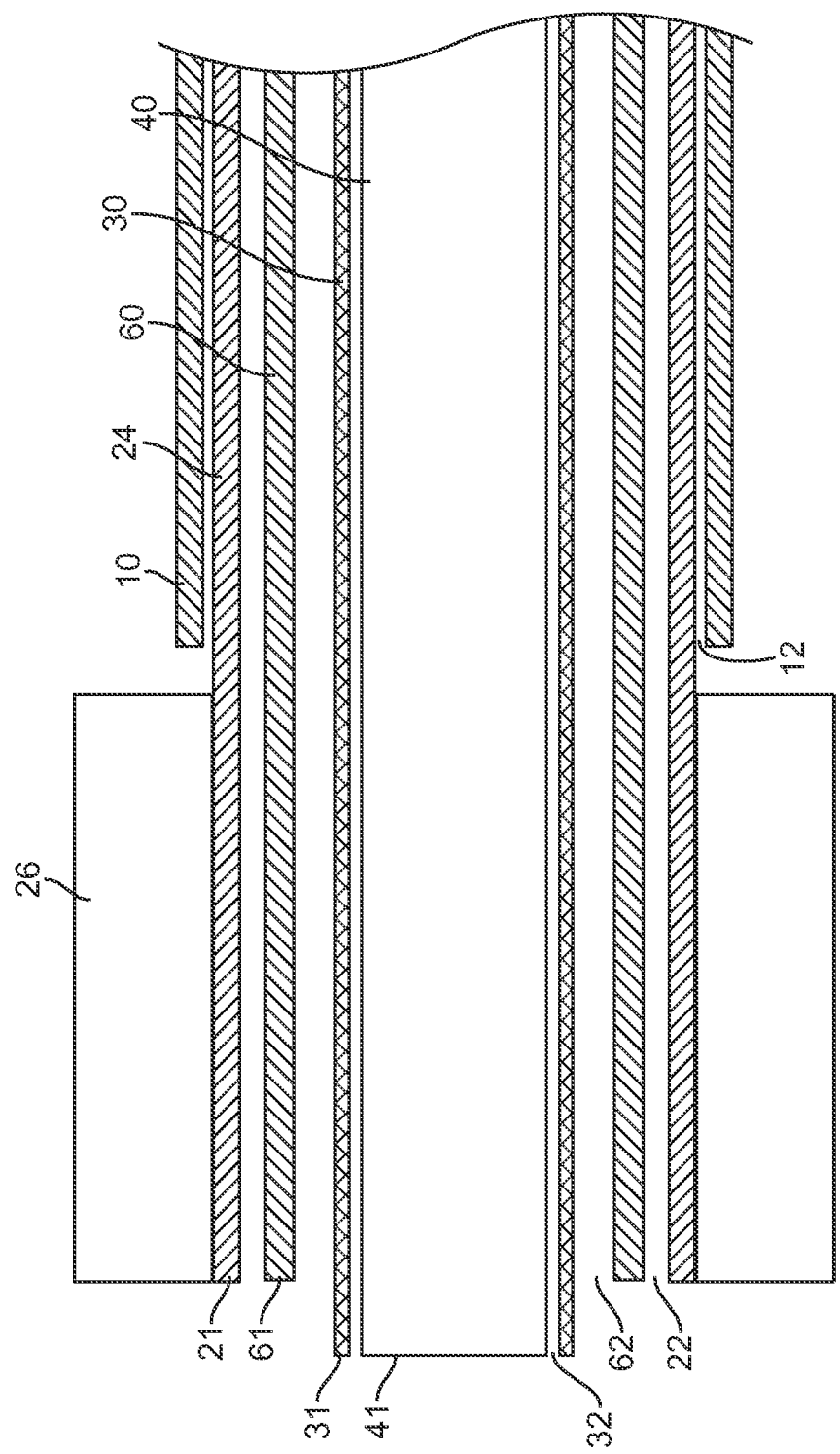

In the radially expanded configuration, the distal end 33 of the hypotube 30 is in a fixed position relative to the guide wire tube 60 so that distally advancing the hypotube 30 causes the distal end 63 of the guide wire tube 60 to advance. Thus, in a second stage of the deploying the elongation apparatus 50, the proximal ends 31, 41 of the hypotube 30 and the mandrel 40 are distally moved towards the proximal ends 21, 61 of the catheter body 24 and the guide wire tube 60, as indicated by arrows 94 in FIG. 4B. Due to the firm engagement between the distal end 33 of the hypotube 30 and the inner surface of the guide wire tube 60, this advancement of the hypotube 30 and mandrel 40 causes the distal end 63 of the guide wire tube 60 to advance distally relative to the distal end 23 of the catheter body 24, as shown in FIG. 5A. As shown in FIG. 5B, the distal ends 31, 41 of the hypotube 30 and mandrel 40 are advanced a desired elongation distance, which, similar to the above-described alternative, may be indicated by a marker (not shown).

Figure 6C:
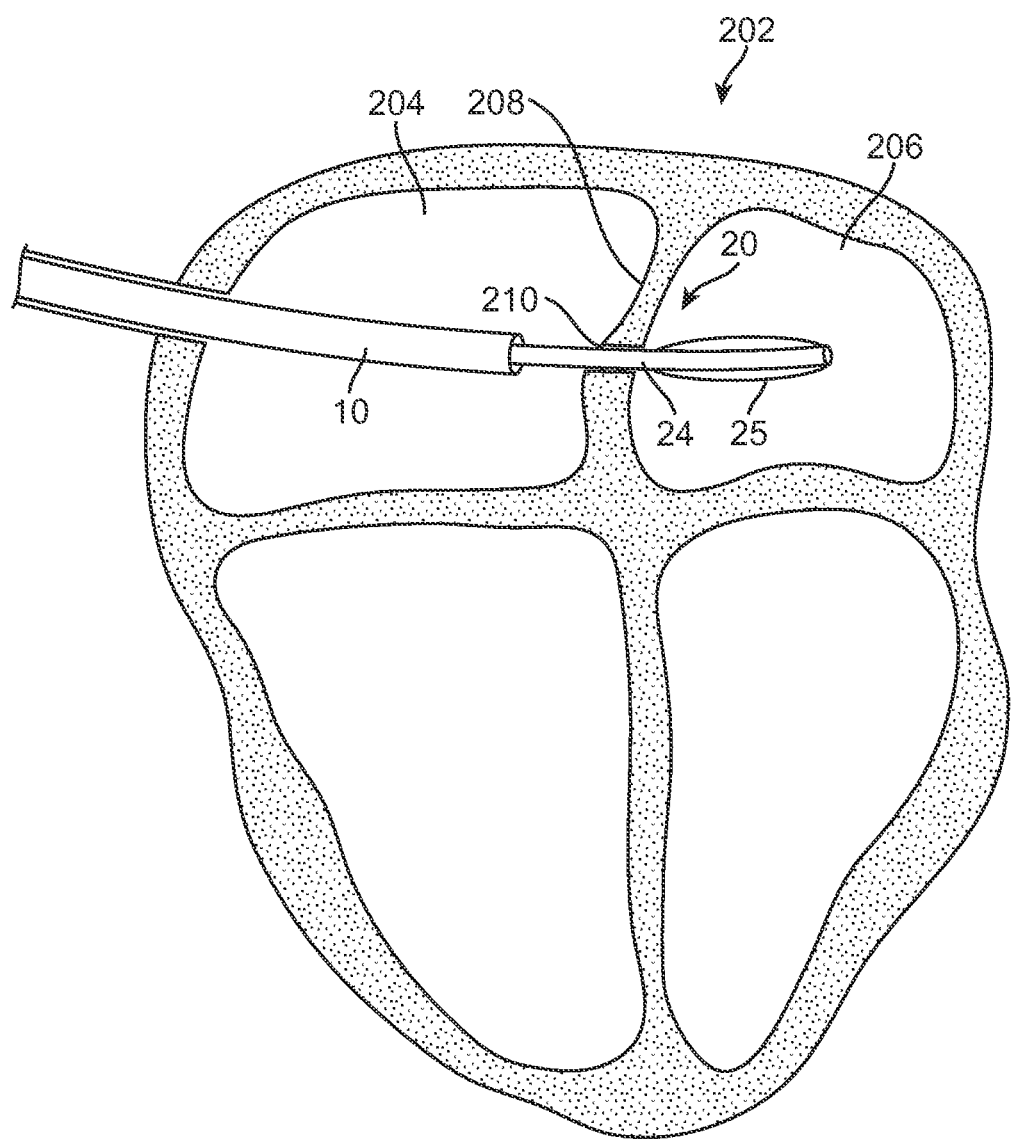

In the illustrated method, the proximal end 61 of the guide wire tube 60 remains fixed relative to the proximal end 21 of the catheter body 24, while the distal end 63 of the guide wire tube 60 advances relative to the distal end 23 of the catheter body 24. Such advancement of the distal and 63 of the guide wire tube 60 may be facilitated by stretchability of the guide wire tube 60 or by slack in the guide wire tube 60 relative to the catheter body 24. In particular, the portion of the guide wire tube 60 that is proximal to the point of engagement between the guide wire tube 60 and the distal end 33 of the hypotube 30 stretches or becomes more taught in order to distally advance the distal end 63 of the guide wire tube 60. The balloon 25 is thus elongated, as shown in FIGS. 5A and 6C. Due to the smaller profile of the elongated balloon 25, retracting the balloon 25 into the lumen 12 of the sheath 10 and/or back through the opening 210 in the atrial septum 208 is facilitated. After the balloon 25 is retracted into the lumen 12 of the sheath 10, the sheath 10 with the balloon 25 therein is safely removed from the patient.

Although particular embodiments have been shown and described, it should be understood that the above discussion is not intended to limit the scope of these embodiments. Various changes and modifications may be made without departing from the scope of the claims. Thus, embodiments are intended to cover alternatives, modifications, and equivalents that may fall within the scope of the claims.

What is claimed is:

1. A balloon elongation apparatus, comprising:
   an elongated member sized to fit within a guide wire lumen of a catheter, the elongated member having a proximal end, a distal end configured to be placed between a radially expanded configuration to firmly engage an inner surface of the guide wire lumen, and a radially relaxed configuration to slide within the guide wire lumen, a lumen extending between the proximal end and the distal end, a larger inner diameter portion, and a smaller inner diameter portion, wherein the smaller inner diameter portion is at the distal end point of the elongated member; and
   an elongated mandrel having a proximal end and a distal end, the elongated mandrel sized to be slidably received within the larger inner diameter portion of the elongated member and configured for radially expanding the distal end of the elongated member when the distal end of the mandrel is advanced from the larger inner diameter portion into the smaller inner diameter portion, wherein the elongated member and the elongated mandrel are both sized and adapted to be inserted through a patient's vasculature and to extend from a treatment site in the patient's heart through and along a length of a lumen of the patient's vasculature to a location outside the patient, the proximal ends of the elongated member and the elongated mandrel extending from a proximal end of the catheter when the distal ends of the elongated member and the elongated mandrel are positioned at the treatment site in the patient's heart.

2. The apparatus of claim 1, wherein the elongated member comprises a tapered transition region between the smaller inner diameter portion and the larger inner diameter portion.

3. The apparatus of claim 1, wherein the distal end of the elongated member comprises a serrated or grooved outer surface.

* * * * *